(12) United States Patent
Driscoll et al.

(10) Patent No.: US 11,149,246 B2
(45) Date of Patent: *Oct. 19, 2021

(54) METHODS FOR CELL LYSIS AND PREPARATION OF HIGH MOLECULAR WEIGHT DNA FROM MODIFIED CELLS

(71) Applicant: Shoreline Biome, LLC, Farmington, CT (US)

(72) Inventors: Mark Driscoll, Wallingford, CT (US); Thomas Jarvie, Branford, CT (US)

(73) Assignee: Shoreline Biome, LLC, Farmington, CT (US)

( * ) Notice: Subject to any disclaimer, the term of this patent is extended or adjusted under 35 U.S.C. 154(b) by 68 days.

This patent is subject to a terminal disclaimer.

(21) Appl. No.: 16/295,306

(22) Filed: Mar. 7, 2019

(65) Prior Publication Data

US 2019/0203168 A1 Jul. 4, 2019

Related U.S. Application Data

(63) Continuation-in-part of application No. 15/854,157, filed on Dec. 26, 2017, now Pat. No. 10,774,322.

(60) Provisional application No. 62/440,171, filed on Dec. 29, 2016.

(51) Int. Cl.
| | |
|---|---|
| *C12Q 1/68* | (2018.01) |
| *C12N 1/06* | (2006.01) |
| *C12Q 1/686* | (2018.01) |
| *C12N 15/11* | (2006.01) |

(52) U.S. Cl.
CPC .............. *C12N 1/06* (2013.01); *C12N 15/11* (2013.01); *C12Q 1/686* (2013.01); *C12N 2310/20* (2017.05)

(58) Field of Classification Search
USPC ........... 435/6.1, 6.11, 6.12, 91.1, 91.2, 91.5; 436/94, 501; 536/23.1, 24.3, 24.33
See application file for complete search history.

(56) References Cited

U.S. PATENT DOCUMENTS

| | | | |
|---|---|---|---|
| 7,238,522 B2 | 7/2007 | Hebel et al. | |
| 10,774,322 B2 * | 9/2020 | Driscoll | C12Q 1/6874 |
| 2002/0022035 A1 * | 2/2002 | Prideaux | A61K 39/102 424/236.1 |
| 2003/0215845 A1 | 11/2003 | Bille | |
| 2005/0014245 A1 | 1/2005 | Hebel et al. | |
| 2005/0026177 A1 | 5/2005 | Urthaler et al. | |
| 2019/0203168 A1 | 7/2019 | Driscoll et al. | |

FOREIGN PATENT DOCUMENTS

| | | |
|---|---|---|
| EP | 2 481 791 A1 | 8/2012 |
| JP | 2006517225 A | 7/2006 |
| JP | 2012157265 A | 8/2012 |
| WO | 99/38962 A2 | 8/1999 |
| WO | 2004083405 A2 | 9/2004 |
| WO | 2005073377 A1 | 8/2005 |
| WO | 2011/070507 A1 | 6/2011 |
| WO | 2011/124708 A1 | 10/2011 |
| WO | 2011153246 A2 | 12/2011 |
| WO | 2016/024263 A1 | 2/2016 |
| WO | 2018/125865 A1 | 7/2018 |

OTHER PUBLICATIONS

Birnboim, H.C. et al., A rapid alkaline extraction procedure for screening recombinant plasmid DNA, Nucleic Acids Research, Nov. 24, 1979, pp. 1513-1523, vol. 7 No. 6.
Christopher Beam, The Rise of Yeast: Why do scientists always experiment on yeast?, Explainer, p. 1-3, May 6, 2009.
Christopher K Lee et al., Factors affecting chemical-based purification of DNA from *Saccharomyces cerevisiae*, Yeast; 29:73-80, Dec. 2, 2011.
Raghunathan, A. et al., Genomic DNA Amplification from a Single Bacterium, Applied and Environmental Microbiology, Jun. 2005, pp. 3342-3347, vol. 71 No. 6, American Society for Microbiology.
Yuan, S. et al., Evaluation of Methods for the Extraction and Purification of DNA from the Human Microbiome, PLoS One, Mar. 23, 2012, pp. 1-13, vol. 7 No. 3.
Mackenzie, B.W. et al., Evaluating variation in human gut microbiota profiles due to DNA extraction method and intersubject differences, Frontiers in Microbiology, 2015, vol. 6 Article 130, pp. 1-11.
"What are Detergents" pp. 1-6. Printed on Feb. 27, 2020.
International Searching Authority, International Search Report and Written Opinion, PCT/US17/68415, dated Mar. 26, 2018.
Antonova, E. et al., Successful CRISPR/Cas9 Mediated Homologous Recombination in a Chicken Cell Line. F1000Research, Feb. 28, 2018; vol. 7, No. 238.
International Search Report for PCT/US20/21184, dated Jun. 9, 2020, p. 4.
Suzuki, H. et al. "Removal of Dodecyl Sulfate from Protein Solution", 1988, Analytical Biochemistry, 172, pp. 259-263.
Supplemental European Search Report for European Application No. EP 17 88 7015, dated Jun. 12, 2020.

\* cited by examiner

*Primary Examiner* — Frank W Lu
(74) *Attorney, Agent, or Firm* — Wiggin and Dana LLP; Anthony D. Sabatelli; Madeleine E. Tavcar (57) ABSTRACT

Disclosed are methods for lysis of cells that combine three lysis steps—(1) heat, (2) detergent and (3) base—into a single step and that can be completed in a short period of time, e.g., a few minutes. The methods combine a normally incompatible detergent and base lysis, allow for simplified removal of detergent after lysis, and importantly, limits damage to DNA, such as shearing, that typically results from separate application of conventional lysis methods, yielding improved quality and quantities of genomic DNA (gDNA).

22 Claims, 5 Drawing Sheets

Average Microbial Abundances at Family/Genus Level

In the Standard Method sample there are 5 Firmicute genuses that are absent or under-represented; Listeria, Blautia, Butyrococcus, Ruminococcus, and Lachnospiracea, while easy to lyse microbes such as Bacteroidetes and Akkermansia are over-represented.

FIGURE 5

METHODS FOR CELL LYSIS AND PREPARATION OF HIGH MOLECULAR WEIGHT DNA FROM MODIFIED CELLS

CROSS-REFERENCE TO RELATED APPLICATIONS

This application is a continuation-in-part of, and claims priority to application number Ser. No. 15/854,157, filed Dec. 26, 2017, which issued as U.S. Pat. No. 10,774,322 on Sep. 15, 2020, and which claims priority to patent application No. 62/440,171, filed Dec. 29, 2016, the contents of each of which are herein incorporated by reference in their entireties.

FIELD OF THE DISCLOSURE

Disclosed are methods for lysing cells to release or extract high molecular weight genomic DNA (gDNA) from inside of the cells. The disclosed methods can be used to prepare DNA for polymerase chain reactions ("PCR") designed to screen cells for large inserts or deletions, for example, to identify cells that have been successfully modified with Clustered Regularly Interspaced Short Palindromic Repeats ("CRISPR").

The disclosed methods combine heat, detergent and base in a single tube and can be completed in a few minutes. The methods combine a normally incompatible detergent and base that facilitate post-lysis removal of detergent without extra steps, and the combination creates unexpected synergies lacking in sequential treatment protocols, that greatly reduces the number of steps and hands-on time, while yielding improved representation of gDNA, for example, from difficult to lyse bacteria in microbiome samples or for applications where large regions of cellular gDNA have been modified.

BACKGROUND OF THE DISCLOSURE

Many cell-based and DNA-based analytical methods require releasing DNA from inside the cell to facilitate analysis. Opening the cells to release the DNA is called 'lysis.' Improved methods for preparing high-quality high molecular weight DNA from cells are needed for PCR-based cell screening methods that identify cells having PCR amplicons longer than a few hundred bases. Conventional methods for cell lysis and rapid DNA preparation often results in shearing (degradation) of the DNA, rendering it useless for PCR amplicons longer than a few hundred bases.

The CRISPR/CAS system is an example of an application where screening requires the identification of PCR amplicons in the kilobase range. This system provides molecular tools that are capable of precisely modifying gDNA inside living cells. Since these modifications are usually introduced without reporter genes, many dozens or hundreds of cell colonies must be screened for the presence or absence of the expected modification so DNA from each of the colonies must be prepared and subjected to PCR. Typically, PCR amplicons are designed to probe DNA in the area of the intended modification, with the PCR designed to reveal an expected change in PCR product size, or contain a sequence that is modified after successful transformation, that differs in susceptibility to restriction enzymes. Based on the efficiency of the CRISPR system, numerous cell colonies will need to be screened to identify clones with the desired DNA modification. If the success rate is low for transformation (for example, 2-5% in induced pluripotent stem cells), hundreds of colonies may need to be screened to find cells with the modified genomic locus.

Thus, in the case of CRISPR-modified cells, which have PCR amplicons in the range of thousands of bases, conventional rapid DNA methods are not readily applicable. While more gentle methods to produce high molecular weight DNA exist, such methods are more cumbersome and time consuming. Therefore, for CRISPR applications, the slow pace of gentle methods would result in keeping large numbers of unscreened cells alive in culture during DNA preparation and screening, which is both time consuming and costly.

Cell lysis methods are also important in microbiome research and applications. Methods used to investigate the microbiome using DNA sequencing techniques first require lysis of microbes so the DNA can be extracted. Most microbiomes are communities of bacteria, archaea and fungi that vary tremendously in their susceptibility to lysis techniques. Differential susceptibility presents a significant problem to researchers, who want to ensure that the toughest (usually Gram-positive) and the easiest (usually Gram-negative) to lyse bacteria are represented in proportion to their population in the original sample. Unfortunately, most microbial lysis protocols work well for some microbes, but poorly for others. Additionally, rapid and simple alkaline lysis techniques used to recover plasmid DNA typically also remove the microbial genomic DNA, which is the target for microbiome screening (Alkaline Lysis opens cells but removes gDNA—Birnboim, H C. and Doly, J., *A rapid alkaline extraction procedure for screening recombinant plasmid DNA, Nucleic Acids Res.* 7(6), 1979, 1513-1524; KOH lysis recovers bacterial genomic DNA—Raghunathan, Arumugham et al. *"Genomic DNA Amplification from a Single Bacterium." Applied and Environmental Microbiology* 71.6 (2005): 3342-3347. PMC. Web. 29 Sep. 2016). There are multiple lysis techniques known in the art that attack cellular integrity based on different biochemical methods, including lysozyme (enzymatic attack on the peptidoglycan cell wall), strong base (chemical attack), detergent (solubilizes cell membranes), bead beating or shaking (mechanical disruption), and heat (Comparison of lysis techniques for microbiome—Sanqing Yuan, Dora B. Cohen, Jacques Ravel, Zaid Abdo, Larry J. Forney. *Evaluation of Methods for the Extraction and Purification of DNA from the Human Microbiome.* PLoS ONE 7(3): e33865. doi:10.1371/journal.pone.0033865; DNA extraction methods affect microbiome profiling results: Wagner Mackenzie B, Waite D W, Taylor M W. *Evaluating variation in human gut microbiota profiles due to DNA extraction method and inter-subject differences. Frontiers in Microbiology.* 2015; 6:130. doi:10.3389/fmicb.2015.00130). Most published or commercially available DNA preparation methods use one or more of these methods to lyse cells, usually in sequential steps that can take a significant amount of time, especially when handling many samples at once. While individual lysis methods are usually sufficient for applications where incomplete or partial lysis yields sufficient DNA for the protocol being performed, they often do not yield DNA from microbiome samples in proportion to the original community, and may fail to lyse certain microbes altogether. For example, a detergent-based lysis may disrupt a subset of cells with weak cell walls and strong cell membranes, but not open detergent-resistant microbes with strong cell walls, leading to under-representation or absence of DNA from detergent resistant cells in the resulting DNA preparation. In another example, bead beating of microbes sufficient to lyse cells with strong cell membranes may shear or destroy DNA released early in the process from easily lysed cells. Additionally, the various methods of lysis tend to be incompatible with each other, and need to be performed sequentially if used in combination. For example, lysozyme will not work in the presence of detergents or strong base. Certain detergents precipitate in the presence of strong base. Bead beating is difficult to combine with a heating process. While individual shortcomings may be overcome by running separate lysis protocols in series, this increases the complexity, time, and cost involved. Importantly, detergents such as sodium dodecyl sulfate (SDS) must be removed after lysis, because SDS interferes with downstream DNA manipulation. Additionally, certain microbes may be resistant to lysis protocols run sequentially, depending on protocol order. For example, certain microbes with tough peptidoglycan cell walls may have an outer envelope of lipid bi-layer that protects from an initial treatment with strong base or lysozyme. Only a simultaneous combination of multiple methods may be effective, or a long sequence of multiple steps, to yield DNA from all microbes in a sample.

The methods disclosed herein streamline lysis for applications and techniques where proportional lysis is desired or necessary, such as microbiome research, by combining multiple lysis methods into a simple, rapid protocol that yields a more representative DNA profile across a sample containing different cellular constituents, such as the microbiome. The methods disclosed herein are also useful for preparing high molecular weight DNA which can be used in screening methods or other PCR-based applications that require PCR products in the kilobase range.

BRIEF SUMMARY

Disclosed are methods for lysis of modified cells, that combine three lysis steps—(1) heat, (2) detergent and (3) base—into a single step and that can be completed in a short period of time, e.g., a few minutes. The methods combine a normally incompatible detergent and base lysis, allows for simplified removal of detergent after lysis, and importantly, yields improved quantities of genomic DNA (gDNA) from modified cells. Further disclosed herein is a method and kit for preparing high molecular weight gDNA suitable for identifying the presence of medium or high molecular weight PCR amplicons, utilizing the cell lysis methods provided herein. This process minimizes DNA damage, and yields gDNA that is sufficient for numerous PCR screenings. Thus, in contrast to other methods of preparing DNA, such as rapid preparation methods that shear the DNA resulting in only small PCR products, the methods described herein result in high molecular weight DNA that enables screening for medium and high molecular weight PCR products, thereby allowing for the preparation of high-quality DNA for applications that include modifications to large regions of cellular gDNA, such as CRISPR applications.

DETAILED DESCRIPTION

The subject matter that is regarded as the invention is particularly pointed out and distinctly claimed in the claims at the conclusion of the specification. The foregoing and other objects, features, and advantages of the invention will be apparent from the following detailed description taken in conjunction with the accompanying drawings.

Disclosed herein are methods for lysing modified cells in a sample to release high molecular weight gDNA from the cells, suitable for PCR amplification of medium or high molecular weight PCR products, comprising: (a) mixing an aqueous solution containing modified biologic cells with (i) an ionic detergent and (ii) a base capable of precipitating the ionic detergent; (b) heating the aqueous solution to at least 50° C. for a time effective to dissolve the ionic detergent; (c) cooling the aqueous solution to 40° C. or less for a time effective to precipitate the ionic detergent; and (d) separating the precipitate from the aqueous solution, wherein DNA released from the biologic cells is present in the aqueous solution after separation of the precipitate.

Genomic DNA inside cells starts off as chromosomes that are millions of bases in size. Purification protocols will shear the DNA, and the more aggressive protocols tend to result in high levels of shearing of DNA into small pieces, such as a conventional rapid boiling preparation protocol. If shearing results in pieces of DNA that are smaller than the desired size of the PCR product, then no PCR product would be amplified. DNA having a size of about 1500 bases and larger is more easily sheared with rapid preparation methods. In general, gDNA needs to be about 5-10 times larger than the desired PCR product, otherwise the DNA will have a cut inside the amplicon target site. PCR products below about 200-300 bases are considered small. 300-1000 bases are typical PCR product sizes. From about 700 bases to 3000 bases or more is considered high molecular weight. High molecular weight gDNA is needed for applications that require a high molecular weight PCR product.

As used herein, the terms "high molecular weight PCR amplicon" and "high molecular weight PCR product" are used interchangeably to mean a PCR amplification product having a size of about 700 bases to about 3000 bases or more.

As used herein, the terms "medium molecular weight PCR amplicon" and "medium molecular weight PCR product" are used interchangeably to mean a PCR amplification product having a size of about 300 bases to about 700 bases.

The methods disclosed herein may further comprising the step of amplifying a PCR product from the DNA released from the biologic cells to determine the presence of the modification. In some embodiments, the PCR product has a size of from about 400 bases to about 3000 bases. In some embodiments, the PCR product has a size of from about 1400 bases to about 2500 bases.

In some embodiments, the genomic DNA of the biological cells is modified from its naturally-occurring state. In some embodiments, the modification includes one or more changes to the sequence of the genomic DNA. In some embodiments, the modification includes one or more epigenetic changes that are not due to changes in DNA sequence. In some embodiments, the modification is a CRISPR modification. In some embodiments, the modification is an agricultural modification of a plant cell.

Simultaneous lysis of multiple samples utilizing the methods disclosed herein allows for highly parallel processing of dozens or even hundreds of samples in a few minutes. This is particularly important for CRISPR applications, where large numbers of cell colonies must be screened to identify those with desired genomic modifications.

In some embodiments, the ionic detergent is selected from the group consisting of: sodium dodecyl sulfate (SDS), N-Lauroylsarcosine sodium salt, or sodium deoxycholate. In some embodiments, the concentration of the ionic detergent is from about 0.1% to about 10% by weight. In some embodiments, the ionic detergent is SDS at a concentration of about 1% by weight. In other embodiments, the ionic detergent is SDS at a concentration of about, 0.1%, 0.25%, 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5% or 10% by weight. The concentration of ionic detergent may be varied based on the type of cell being lysed and can be determined using methods known in the art. For example, 0.25% by weight SDS may be used cells that are easy to lyse, and 10% by weight SDS may be used for plant cells, which are typically difficult to lyse.

In some embodiments, the base is selected from the group consisting of: potassium hydroxide (KOH), lithium hydroxide (LiOH), sodium hydroxide (NaOH), rubidium hydroxide (RbOH), cesium hydroxide (CsOH), calcium hydroxide $(Ca(OH)_2)$, strontium hydroxide $(Sr(OH)_2)$, and barium hydroxide $(Ba(OH)_2)$. In some embodiments, the concentration of the base is from about 0.05 molar to about 1 molar. In some embodiments, the base is potassium hydroxide (KOH) at a concentration of about 0.2 molar. In some embodiments, the detergent is combined with a base that precipitates the detergent at low temperature, but permits the detergent to dissolve at high temperature.

In some embodiments, the ionic detergent is sodium dodecyl sulfate (SDS) at a concentration of 1% by weight and the base is an aqueous solution containing potassium hydroxide (KOH) at a concentration of 0.2 molar.

In some embodiments, the heating is conducted at a temperature range of from about 50° C. to about 100° C., causing the precipitate to dissolve. In some embodiments, the heating is conducted at a temperature of about 65° C. In some embodiments, the heating is conducted at a temperature of about 95° C. In some embodiments, the heating is conducted for at least 1 minute. In some embodiments, the heating is conducted at about 95° C. for about 5 minutes. In other embodiments, a temperature in the range of from about 50° C. to about 94° C. may be used to heat for durations greater than 5 minutes, and a temperature in the range of from about 95° C. to about 100° C. may be used to heat for durations shorter than 5 minutes.

In some embodiments, the cooling is conducted at a temperature in the range of from about 4° C. to about 40° C. In some embodiments, the cooling is conducted at a temperature of about 20° C. to about 25° C. In some embodiments, the cooling is conducted for at least 30 seconds.

In some embodiments, the separating is conducted by a method selected from the group consisting of: centrifugation, filtration, gravity settling.

In some embodiments, the biologic cells originate from a sample selected from the group consisting of: feces, cell lysate, tissue, blood, tumor, tongue, tooth, buccal swab, phlegm, mucous, wound swab, skin swab, vaginal swab, or any other biological material or biological fluid originally obtained from a human, animal, plant, or environmental sample, including raw samples, complex samples, mixtures, and microbiome samples.

In some embodiments, the biologic cells originate from an organism selected from the group consisting of: multicellular organisms, unicellular organisms, plants, prokaryotes, eukaryotes, microbes, bacteria, archaea, protozoa, algae and fungi.

Example 1: 16S rRNA Gene Microbiome Sequencing

DNA located inside cells, such as bacteria and archaea in a microbiome, can be released by lysing the cells. To investigate a microbiome, cells in the target microbiome are lysed, after which the resulting DNA in this description can either be sequenced directly ('shotgun' sequencing), or used as template in PCR amplification targeting a genetic region such as the 16S rRNA gene, present in all bacteria and archaea. The 16S gene is used as an example herein because it can be used as a 'fingerprint' identification method for microbes, requiring ~1000× less sequencing than the shotgun method. Microbes can be identified using their 16S rRNA gene sequence, which varies slightly in most, if not all, bacteria and archaea. The variation in 16S gene sequence means that individual species of bacteria and archaea have characteristic DNA variations ('fingerprints') in the 16S rRNA gene that serve as identifiers for those species or strains. Kits, protocols and software enable comprehensive fingerprinting of the microbes in a sample, and permits simultaneous 16S rRNA fingerprinting of many samples at once, at high resolution, using the full length 16S rRNA gene (see, for example, U.S. patent application Ser. No. 15/372, 588 titled "Methods for DNA Preparation for Multiplex High Throughput Targeted Screening" by Mark Driscoll and Thomas Jarvie, that is incorporated herein by reference in its entirety). Known microbes can be identified after sequencing by mapping the DNA sequence of the 16S gene to a database of known reads. Unknown microbes will contain 16S DNA sequences that are different from any of the microbes in the database, but can be tracked using their unique 16S sequence. In addition, the number of reads obtained for each microbe in a sample can reveal the relative abundances of each microbe in a sample. The relative abundance of specific microbes can be an important indicator of the state of each individual microbiome. Lysis techniques that change relative abundances of microbes, or leave out DNA from certain microbes altogether, can lead to sequencing results that incorrectly characterize the state of the microbiomes being studied. The methods described herein can be used to achieve the correct relative abundances of microbes from a sample.

The lysis process can be used for 'shotgun' microbiome sequencing as well, where the DNA is subjected to sequencing after lysis without 16S rRNA gene amplification. The shotgun method is used when investigators want to read all DNA sequences in a sample, not just the 16S gene from bacteria and archaea. For example, high depth shotgun microbiome DNA sequencing may reveal the full DNA genomic sequence from unknown bacteria/archaea, as well as fungi, or multicellular eukaryotes, viral DNA, or any other DNA containing organisms. Since a full bacterial genome can be millions of bases long (thousands of times larger than the 16S gene), fungal genomes can be more than a hundred million bases, and eukaryotic genomes can be billions of bases long, a shotgun microbiome profile can require thousands of times more sequencing than a 16S rRNA gene microbiome profile, with correspondingly greater time and costs. Although only the 16S profiling method is discussed in this example, the lysis protocol described herein provides the same advantages to both shotgun and 16S rRNA microbiome sequencing approaches.

The following is an example of the disclosed methods for the 16S rRNA gene microbiome sequencing approach:

Step 1. A microbiome sample was dispersed into an aqueous solution containing 2% by weight of sodium dodecyl sulfate (SDS).

Step 2. 0.4M KOH was added and SDS detergent precipitated as white flocculent. In this example, the detergent (1% SDS) is precipitated by the base (0.2M KOH).

Step 3. The tube was capped and heated (temperature can range from about 50° C. to about 100° C.). SDS dissolves at temperatures above 50° C. Heat and KOH attack the peptidoglycan cell wall, and SDS solubilizes membranes that protect microorganisms from the damaging effects of the KOH and heat. This combination of steps is synergistic, because sequential exposure to KOH, SDS, and heat, in contrast to the combined exposure described here, may not yield the same results because of the way that microbial cell walls and membranes are structured. Heat actually allows SDS to work in the presence of strong base, resulting in a unique simultaneous combination of three different lysis techniques.

Step 4. After heating, the sample was brought back to room temperature (e.g., below 40° C.) to precipitate the SDS detergent.

Step 5. The sample was centrifuged briefly to pelletize the SDS detergent (no additions necessary, rapid removal of detergent).

Step 6. The supernatant was moved to tube containing 500 mM Tris buffer or equivalent, pH 8.5. The released DNA is now ready for analysis by 16S rRNA PCR (as described below), or can be stored or purified further for other uses.

Figure 1A:
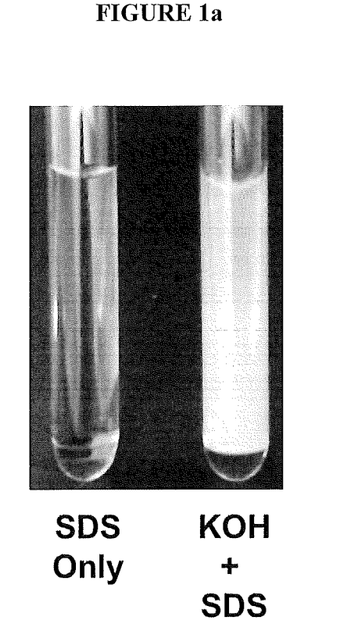
FIG. 1a shows the white SDS precipitate in the potassium hydroxide (KOH+SDS) tube (right), at room temperature. The tube at left shows 1% SDS in the absence of KOH as a clear solution.
Figure 1B:
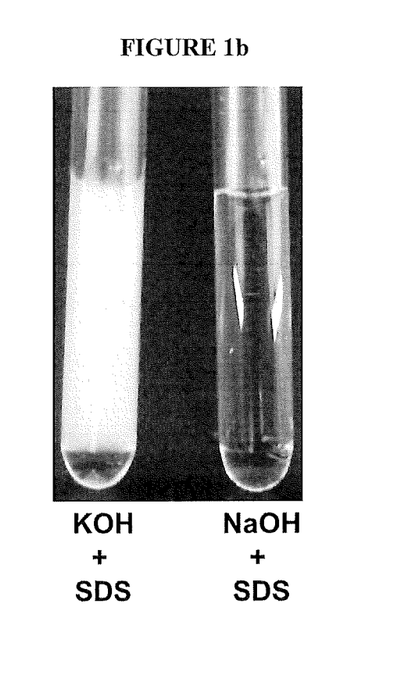
FIG. 1b shows the white SDS precipitate in the potassium hydroxide (KOH+SDS) tube (left), at room temperature. The tube at right shows 1 SDS in the presence of NaOH as a clear solution, demonstrating that NaOH does not precipitate SDS.
Figure 2:
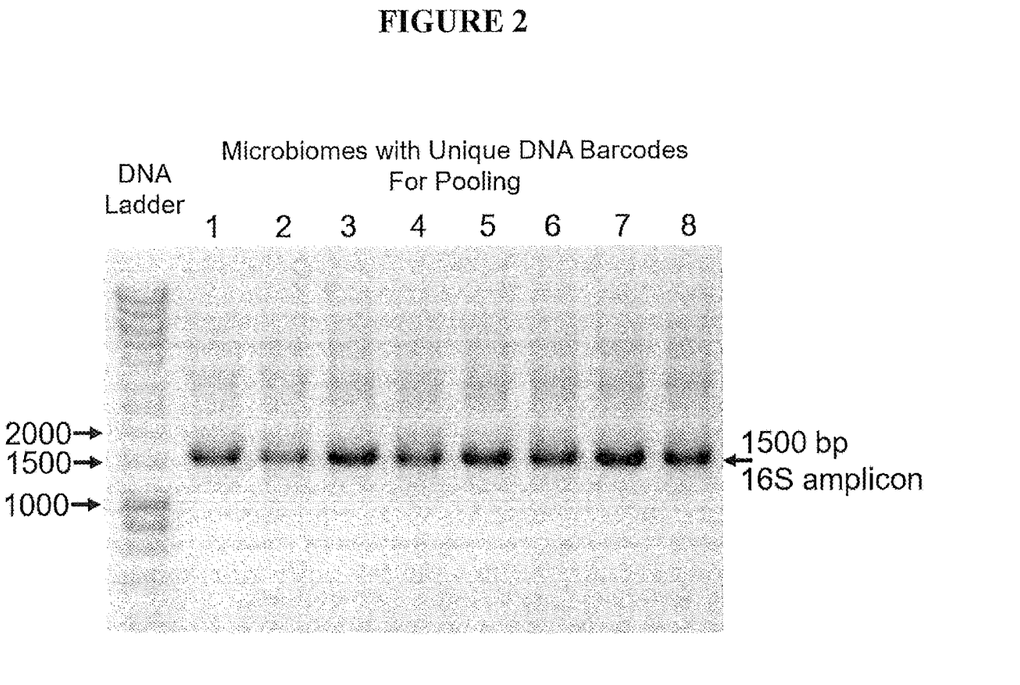

Each DNA sample was subjected to PCR amplification a method which assigns unique DNA barcodes to each sample. An example PCR reaction for 8 different microbiomes is shown in FIG. 2 where human fecal samples 1-8 were lysed according to the protocol described above in Steps 1-6, or by a standard protocol with sequential detergent/bead beating steps. Each sample was PCR amplified using primers to the 1500 bp 16S rRNA gene, with a different DNA barcode for each sample. Samples were pooled for DNA sequencing after PCR. Since the reads from each sample contained a unique identifying DNA barcode, they can be sorted by sample after sequencing. Reads output by the sequencer are sorted by sample using barcodes and mapped to a database to identify known microbes, unknown microbes, and their relative proportion in each sample.

Figure 3:
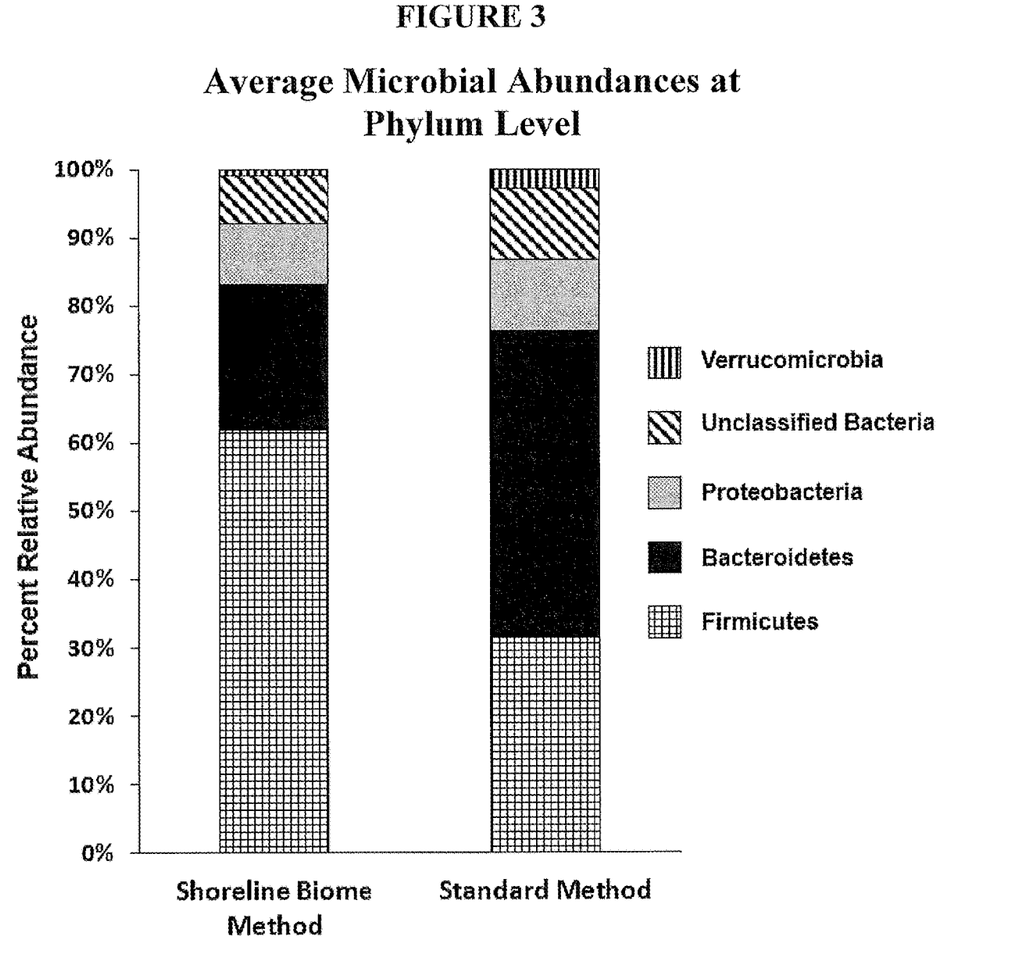
FIG. 3 is a graph showing a comparison of average microbial abundances at phylum level in multiple samples lysed using sequential lysis steps of detergent and bead beating or the combined lysis method described herein. There is a higher abundance of the more difficult to lyse Firmicutes using the Shoreline Biome method.

After sorting by barcode into sample of origin, identification by genus, and quantitation of the number of reads for each genus by software analysis of the reads, the reads for each microbiome were compared. Depending on the experimental design, there are a number of ways the output could be compared. In FIG. 3, the quantity of each microbe in a microbiome is included in a 100% stacked bar plot for two samples. This method allows for simple, direct comparison of microbiomes. Other useful comparisons include phylum level differences, species or strain level differences, or other taxonomic levels.

For multiple samples, a standard method using sequential lysis steps of detergent and bead beating was compared to the combined lysis method described herein. As shown in FIG. 3, Gram-positive Firmicutes increased in abundance from ~30% to over 60% of the microbiome. Firmicutes are Gram positive bacteria with strong cell walls that tend to be difficult to lyse. This demonstrates that the lysis method described herein is better at lysing microbes with strong cell walls. Easy to lyse Bacteriodetes and Verrucomicrobia phyla decreased proportionally, as would be expected when using a 100% stacked bar plot.

Figure 4:
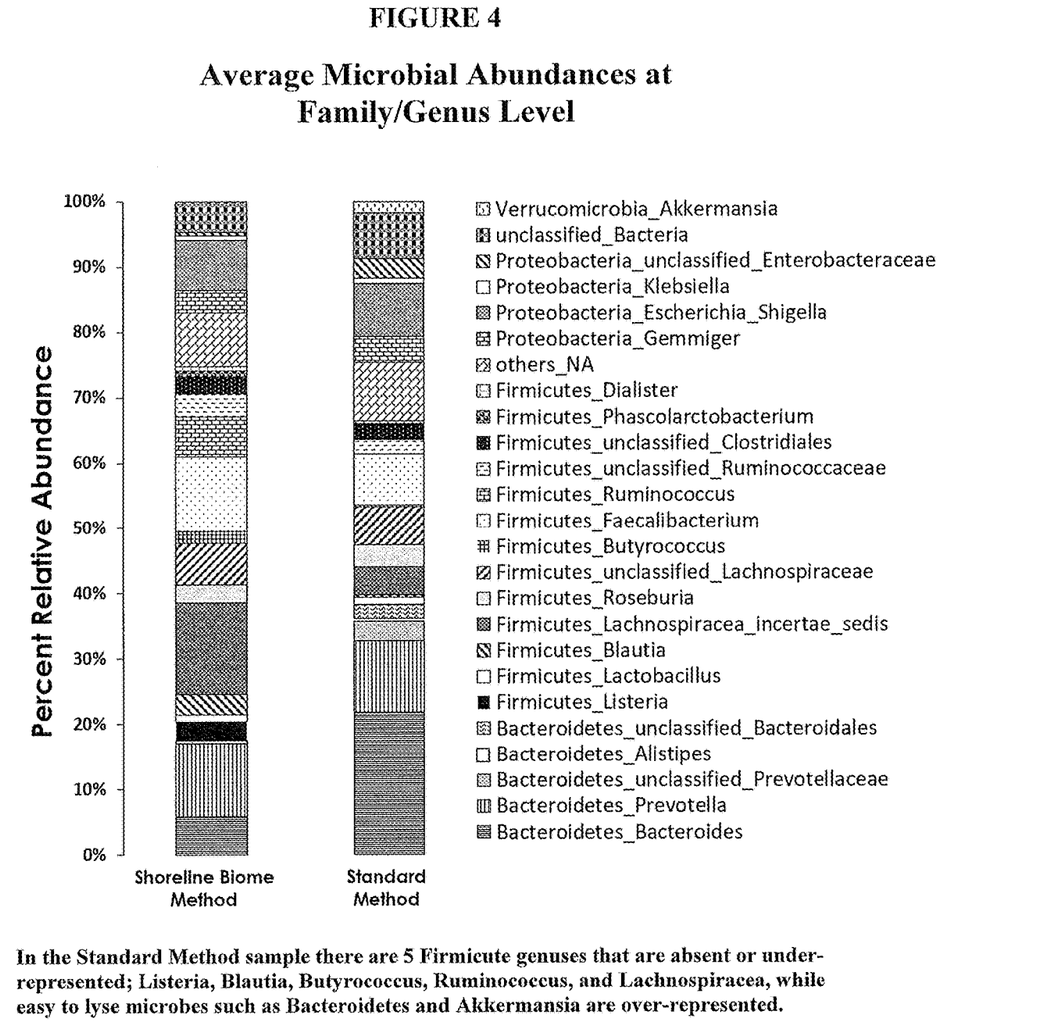
FIG. 4 is a graph showing a comparison of average microbial abundances at genus level in multiple samples lysed using sequential lysis steps of detergent and bead beating or the combined lysis method described herein. This demonstrates that the phylum level abundances in FIG. 3 correspond to the appearance of an increased quantity and diversity of Firmicutes at the genus level.

FIG. 4 depicts average abundances at the genus level for the same samples shown in FIG. 3. FIG. 4 is a higher-resolution view of the Firmicutes that are under-represented using the standard method using sequential lysis steps of detergent and bead beating. The bar plot of genus level differences in abundance show that there are five Firmicutes genuses under-represented using the standard sequential lysis method (*Listeria, Blautia, Lachnospiracea Incertae Sedis, Butyrococcus, Ruminococcus*), and the relative representation of the *Bacteroides* and *Akkermansia* is artificially high using the standard method. This parallels the phylum level differences in FIG. 3, while showing that individual Firmicutes genus levels can be significantly under-represented using the standard method.

Example 2: Preparation of DNA from CRISPR-Modified Cells

This Example describes an application of the disclosed lysis process for extracting high molecular weight gDNA from inside cells for use in PCR reactions to identify cells that have been successfully CRISPR modified. This Example utilizes: (a) Lysis Solution 1-1% by weight SDS; (b) 70% ethanol; (c) 0.4M NaOH; and (d) Purification Buffer, using the following method:

Step 1. At least one or two cells colonies were selected for purification. In an embodiment, the cell colonies are preferably whole well.

Step 2. The cell colonies were aspirated from the bottom of the plate with 100 µL of culture media.

Step 3. Once all cell samples were collected, the cells were pelleted in a minifuge for approximately two minutes. In an embodiment, the cells may be centrifuged for 2 minutes at a rate of 1500 RCF, to pellet the cells in the bottom of the tube.

Step 4. Culture media was aspirated, avoiding cell pellets in the bottom of the tube, and discarded.

Step 5. 50 µL of Lysis Solution 1 was added to each tube containing a cell pellet.

Step 6. The cell pellet was then re-suspended in Lysis Solution 1 by pipetting gently up and down until the pellet dispersed.

Step 7. 50 µL of 0.4M NaOH was added to each tube Lysis Solution 1/sample mix, forming a precipitate.

Step 8. Samples were capped tightly, the PCR machine was set for proper tube height, and the lid was closed and locked.

Step 9. Samples were heated to 95° C. for 5 minutes, causing the precipitate to dissolve. In other embodiments, a range of 50° C.-94° C. may be used durations greater than 5 minutes, and 95° C.-100° C. may be used durations shorter than 5 minutes.

Step 10. After incubation, samples were allowed to cool to room temperature before unlocking the PCR lid, with failure to cool properly resulting in lids popping off the tubes.

Step 11. While cooling the samples, the Purification Buffer tube was vortexed for 15 seconds on max speed, to re-suspend any brown magnetic beads that may have settled.

Step 12. 100 μL of Purification Buffer was added to the lysate tube, and pipetted up and down to gently mix.

Step 13. The solution was incubated for 3 minutes at 50° C. to allow DNA to bind to beads.

Step 14. The solution was placed on a magnetic rack to pellet the beads with bound DNA to the side of the tubes. In an embodiment, this may be done for about 60 seconds.

Step 15. Once all beads were pelleted, all supernatant was slowly removed and discarded, with great care taken to avoid aspirating beads.

Step 16. Tubes were removed from the magnetic rack, and 100 μL of 70% ethanol was added, at room temperature, to each tube. The beads were then re-suspended by pipetting gently up and down.

Step 17. The tubes were returned to the magnetic rack and beads were allowed to pellet, for approximately 30 seconds.

Step 18. Residual ethanol was pipetted off the tubes, and they were allowed to air dry for approximately 2-3 minutes. It should be noted that over-drying beads would cause eluting DNA to become more difficult, so the bead pellets must be observed to ensure that the ethanol is mostly gone, while at the same time the bead pellets should not begin to shrink or crack. 2-3 minutes were observed as the ideal amount of drying time, but other times are contemplated and may be necessary, depending on environmental conditions.

Step 19. The tubes were removed from the magnetic rack.

Step 20. 15 μL of 1×TE buffer was added to the tubes, being briefly pipetted up and down to re-suspend the beads. This resulted in a solution that is brown in color, to reflect beads that are mixed homogeneously throughout.

Step 21. The solution was incubated for 2 minutes at room temperature.

Step 22. The tubes were placed on the magnetic rack for 30-60 seconds, to pellet the magnetic beads.

Step 23. Supernatant containing eluted DNA was transferred into clean, labeled microcentrifuge tubes on ice, thereby avoiding pelleted beads.

Step 24. Tubes were removed from the magnetic rack and 10 μL 1×TE buffer was added to the tubes, being briefly pipetted up and down to re-suspend the beads. This resulted in a solution brown in color to reflect the beads mixed homogenously throughout.

Step 25. The solution was incubated for 2 minutes at room temperature.

Step 26. The tubes were placed a magnetic rack for 30-60 seconds to pellet magnetic beads.

Step 27. Supernatant was combined with previously eluted DNA, avoiding pelleted beads.

Figure 5:
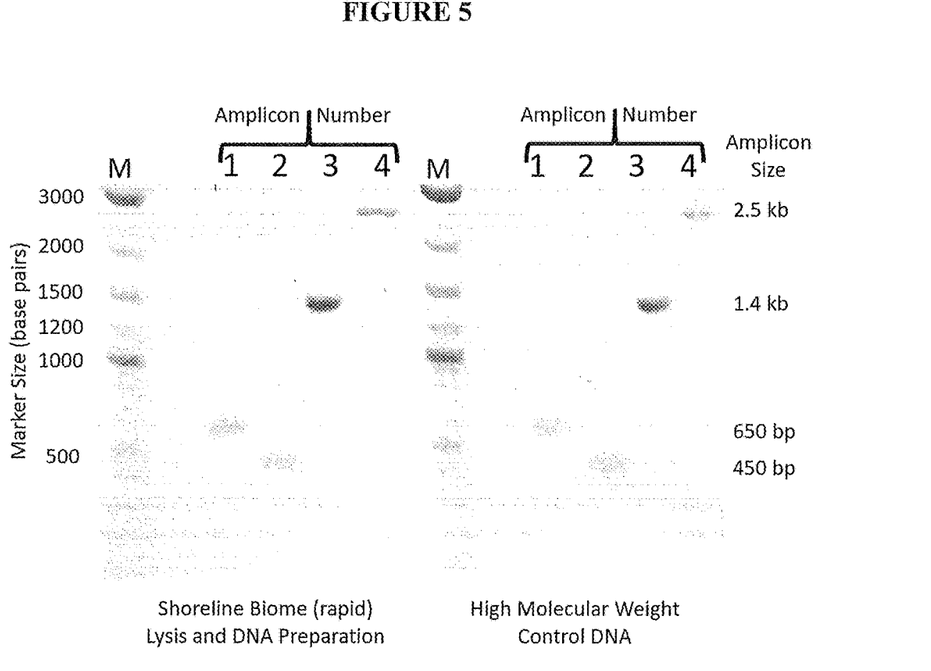
FIG. 5 depicts PCR amplicons prepared from DNA purified from CRISPR-modified cells, compared to amplicons prepared using a high molecular weight control DNA.

Step 28. 5-10 μL was used to purify DNA in a PCR reaction as shown in FIG. 5.

FIG. 5 depicts PCR amplicons prepared from DNA purified from large molecular weight cells as described in this Example. As illustrated, the DNA quality is sufficient for long PCR amplicons. The left side of FIG. 5 illustrates PCR amplicons prepared from DNA that is purified from cells with the rapid lysis method described in this Example. The right side illustrates to amplicons prepared using a high molecular weight control DNA. Four amplicons were tested, ranging in size from 450 base pairs to 2500 base pairs (representing high molecular weight PCR amplicons and medium molecular weight amplicons), indicated by the sizes on the right side of the Figure. Reference DNA marker "M" is shown on the left side of each panel. This PCR result illustrates that the DNA quality was sufficient for production of the expected amplicons in each case.

One or more embodiments of the present invention have been described. Nevertheless, it will be understood that various modifications may be made without departing from the spirit and scope of the invention. Accordingly, other embodiments are within the scope of the following claims.

What is claimed is:

1. A method for releasing genomic DNA from modified biologic cells in a sample by lysing the modified biologic cells, comprising the sequential steps of:
   a) producing a mixture solution by mixing an aqueous solution containing the modified biologic cells from the sample with (i) an amount of an ionic detergent, and (ii) an amount of a base such that the ionic detergent and the base in the mixture solution are at concentrations effective for releasing the genomic DNA from the modified biologic cells by lysing the modified biologic cells after the ionic detergent is dissolved in the mixture solution, wherein the ionic detergent is sodium dodecyl sulfate (SDS) and the base is potassium hydroxide (KOH);
   b) heating the mixture solution to at least about 50° C. for a time such that the ionic detergent is dissolved in the mixture;
   c) cooling the mixture solution to 40° C. or less for a time effective to precipitate the ionic detergent, thereby producing a precipitate comprising the ionic detergent; and
   d) separating the precipitate comprising the ionic detergent from the mixture solution,
   wherein the biologic cells contain one or more modifications, wherein the genomic DNA released from the modified biologic cells is present in a solution generated by said separating the precipitate comprising the ionic detergent from the mixture solution; and wherein the genomic DNA released from the modified biologic cells is ready for analysis, polymerase chain reaction (PCR), sequencing, purification, or storage.

2. The method of claim 1, further comprising a step of amplifying a PCR product from the genomic DNA released from the modified biologic cells to determine the presence of the one or more modifications.

3. The method of claim 2, wherein the PCR product has a size from about 400 bases to about 3000 bases.

4. The method of claim 3, wherein the PCR product has a size from about 1400 bases to about 2500 bases.

5. The method of claim 1, wherein the genomic DNA of the modified biologic cells contains the one or more modifications.

6. The method of claim 5, wherein the one or more modifications are selected from the group consisting of: a change in the sequence of the genomic DNA, an epigenetic change of the genomic DNA, and both a change in the sequence of the genomic DNA and an epigenetic change of the genomic DNA.

7. The method of claim 5, wherein the one or more modifications comprise a clustered regularly interspaced short palindromic repeat (CRISPR) modification in the genomic DNA of the modified biologic cells.

8. The method of claim 1, wherein the ionic detergent of the mixture solution in step b) is from about 0.1% by weight to about 10% by weight.

9. The method of claim 1, wherein the ionic detergent of the mixture solution in step b) is about 1% by weight.

10. The method of claim 1, wherein the base of the mixture solution in step b) is from about 0.05 molar to about 1 molar.

11. The method of claim 1, wherein the base of the mixture solution of step b) is about 0.2 molar.

12. The method of claim 1, wherein the ionic detergent of the mixture solution of step b) is 1% by weight and the base of the mixture solution of step b) is 0.2 molar.

13. The method of claim 1, wherein the at least about 50° C. in step b) is a temperature range from at least about 50° C. to about 100° C.

14. The method of claim 13, wherein step b) is conducted at a temperature of about 95° C.

15. The method of claim 14, wherein the time conducted in step b) is at least 0.25 minutes.

16. The method of claim 14, wherein the time conducted in step b) is about 5 minutes.

17. The method of claim 1, wherein the 40° C. or less in step c) is a temperature range from about 4° C. to about 40° C.

18. The method of claim 17, wherein the about 4° C. to 40° C. is a temperature range from about 20° C. to about 25° C.

19. The method of claim 18, wherein the time conducted in step c) is at least 0.25 minutes.

20. The method of claim 1, wherein step d) is conducted by a method selected from the group consisting of: centrifugation of the mixture solution, filtration of the mixture solution, and gravity settling of the mixture solution.

21. The method of claim 1, wherein the modified biologic cells originate from a sample selected from the group consisting of: feces, cell lysate, tissue, blood, tumor, tongue, tooth, buccal swab, phlegm, mucous, wound swab, skin swab, vaginal swab, or any other biological material or biological fluid originally obtained from a human, animal, plant, or environmental samples, raw samples, complex samples, mixtures of samples, and microbiome samples.

22. The method of claim 1, wherein the modified biologic cells originate from an organism selected from the group consisting of: multicellular organisms, unicellular organisms, prokaryotes, eukaryotes, microbes, bacteria, archaea, protozoa, algae, fungi and viruses.

* * * * *